United States Patent [19]

Hwang

[11] Patent Number: 4,872,875
[45] Date of Patent: Oct. 10, 1989

[54] PROSTHETIC HEART VALVE

[75] Inventor: Ned H. C. Hwang, Houston, Tex.

[73] Assignee: Carbon Implants, Inc., Austin, Tex.

[21] Appl. No.: 296,428

[22] Filed: Jan. 28, 1989

[51] Int. Cl.[4] .................................................. A61F 2/24
[52] U.S. Cl. .................................... 623/2; 137/512.1; 137/527
[58] Field of Search ................. 623/2; 137/512.1, 527, 137/527.8

[56] References Cited

U.S. PATENT DOCUMENTS

| | | | |
|---|---|---|---|
| 4,011,601 | 3/1977 | Clune et al. | 623/2 |
| 4,306,319 | 12/1981 | Kaster | 623/2 |
| 4,308,624 | 1/1982 | Klawitter | 623/2 |
| 4,326,304 | 4/1982 | Klawitter | 623/2 |
| 4,423,525 | 1/1984 | Vallana et al. | 623/2 |
| 4,425,670 | 1/1984 | Figuera | 623/2 |
| 4,484,365 | 11/1984 | Murquet et al. | 623/2 |
| 4,512,366 | 4/1985 | Lewis | 623/2 X R |
| 4,535,484 | 8/1985 | Marconi | 623/2 |
| 4,601,719 | 7/1986 | Totten | 623/2 |
| 4,605,408 | 8/1986 | Carpentier | 623/2 |
| 4,775,378 | 10/1988 | Knoch et al. | 623/2 |

FOREIGN PATENT DOCUMENTS

| | | | |
|---|---|---|---|
| 0211576 | 2/1987 | European Pat. Off. | 623/2 |
| 1304810 | 4/1987 | U.S.S.R. | 623/2 |

Primary Examiner—Ronald L. Frinks
Attorney, Agent, or Firm—Fitch, Even, Tabin & Flannery

[57] ABSTRACT

A heart valve of the bi-leaflet or monoleaflet type having improved reductions in drag on blood flow through the fully opened heart valve. The leaflets are pivotally mounted in a heart valve body for movement between closed and opened positions. The leaflets have opposed inflow and outflow surfaces. The inflow surface includes a concave region located downstream of the leaflet pivot axis, and a convex region located downstream of the concave region. The outflow surface of the leaflets is generally convex, at least in that portion directly opposing the concave and convex regions of the inflow surface. The angle of leaflet opening is controlled to values ranging between 70° and about 89°.

14 Claims, 2 Drawing Sheets

PROSTHETIC HEART VALVE

BACKGROUND OF THE INVENTION

The present invention pertains to heart valve prostheses and in particular, to prosthetic heart valve using pivotable valve members, including bi-leaflet valves.

DESCRIPTION OF THE PRIOR ART

Various types of heart valve prostheses have been developed which operate hemodynamically as a result of the pumping action of the heart. Among the types of heart valves which have been developed are valves having single occluders which pivot along an eccentric axis to open and close the heart valves, such as that described in U.S. Pat. Nos. 4,011,601, 4,423,525 and 4,425,670, and bi-leaflet heart valves, such as those described in U.S. Pat. Nos. 4,484,365 and 4,535,484. The above-mentioned patents illustrate various arrangements for pivotally connecting the valve members or occluders to a valve body and disclose occluders of a variety of shapes. However, most of these designs have never become commercial because of some shortcoming, and the need continues for improved prosthetic heart valves for permanent implantation into the human heart.

In its open position, a prosthetic valve should provide a passageway which is large and which has good flow characteristics so that blood flows freely therethrough without adverse boundary layer separation and with a minimum of drag. The heart valve should be responsive to blood flow to quickly open during the pumping stroke of the heart and to close quickly when the heart relaxes to prevent substantial regurgitation of the blood. The opening and closing of the valve should be sufficiently soft so that the patient is not disturbed by the sounds produced. The heart valve must, of course, be biocompatible and thrombo-resistant, and in this regard, it is important that all surfaces be well washed by blood to prevent stagnation which might lead to eventual clotting. Furthermore, the action of the valve should be such that it does not cause hemolysis (breaking of blood cells), and of course, the heart valve should be constructed to withstand countless openings and closings.

SUMMARY OF THE INVENTION

The present invention provides heart valves having the aforementioned desirable characteristics wherein the valve occluders are designed to eliminate boundary layer separation adjacent their surfaces in the open position and thereby minimize drag, resulting in excellent blood flow characteristics therethrough.

These and other objects of the present invention, which will become apparent from studying appended the description and accompanying drawings, are provided in a prosthetic heart valve for allowing blood flow therethrough in a downstream direction. The valve comprises:

a generally annular valve body having an interior surface defining a central passageway through which blood flows, a pair of occluders proportioned to be pivotally received within said valve body and to move between an open position wherein downstream flow of blood is permitted and a closed position wherein the reverse flow of blood in an inflow direction is blocked, said occluders each having a pair of opposite lateral edges respectively extending between a minor mating edge and a major arcuate edge and having major inflow and outflow surfaces, cooperative pivotal mounting means incorporated in said occluders in the regions of each lateral edge and in said valve body in its interior surface region which cooperate to establish generally pivotal movement of said occluders about a pair of parallel pivot axes, said occluders each having an inflow surface formed with a concave region of two-dimensional curvature and with a generally convex region of two-dimensional curvature, said concave surface region being spaced downstream from said pivot axis in said open position and being curved about a straight line which is generally parallel to said pivot axis, said convex region being spaced further from said pivot axis than said concave region, and said occluders being installed in said annular valve body and constructed so that said occluders have an angle of opening of about 70° to about 89° in said fully open position with said outflow surface regions lying generally adjacent the centerline through said central passageway, and so that, in the closed position, said mating edges of said occluders generally abut each other and said arcuate edges of said occluders abut said valve body interior surface. Preferably, the angle of opening of the leaflets has a value ranging between about 70° and about 85°, and most preferably, has an angle ranging between about 77° and about 83°.

In addition to a bi-leaflet heart valve of the above type, other objects and advantages, according to the present invention, are provided in a prosthetic heart valve for allowing blood flow therethrough in a downstream direction. The valve comprises:

a generally annular valve body having an interior surface defining a central passageway through which blood flows, occluder means proportioned to be pivotally received within said valve body and to move between an open position wherein downstream flow of blood is permitted and a closed position werein the reverse flow of blood in an inflow direction is blocked, said occluder means having a major arcuate edge and having major inflow and outflow surfaces, cooperative pivotal mounting means incorporated in said occluder means lateral edge and in said valve body in its interior surface region which cooperate to establish generally pivotal movement of said occluder means about a pivot axis,:

said occluder means having an inflow surface formed with a concave region of two-dimensional curvature and with a generally convex region of two-dimensional curvature, said concave surface region being spaced downstream from said pivot axis in said open position and being curved about a straight line which is generally parallel to said pivot axis, said convex region being spaced further from said pivot axis than said concave region, and said occluder means being installed in said annular valve body so as to have an angle of opening of about 70° to about 89° in said fully open position, and so that, in the closed position, said major arcuate edge of said occluder means abuts said valve body interior surface. The angle of opening is preferably limited to between about 70° and about 85°, and most preferably, lies between about 77° and about 83°.

BRIEF DESCRIPTION OF THE DRAWINGS

In the drawings, wherein like elements are referenced alike.

DETAILED DESCRIPTION OF THE PREFERRED EMBODIMENTS

FIGS. 1–5 and 6–8 show first and second embodiments of heart valve prostheses constructed according to principles of the present invention. The first heart valve, generally designated at 10 is of a bi-leaflet construction, whereas the second embodiment generally designated by the numeral 110, is of a monoleaflet construction.

Both embodiments attain numerous advantages as will be described herein. For example, both heart valves provide an improved flow when the valve is in a fully opened position and eliminate boundary layer separation at major surfaces of the leaflets, thus minimizing drag, while providing excellent wash characteristics so as to prevent stagnation which might lead to eventual clotting. In addition, both embodiments of the heart valve provide a rapid response upon opening and closing, without hemolysis or the like injury to blood cells fowing through the valve.

Figure 1:
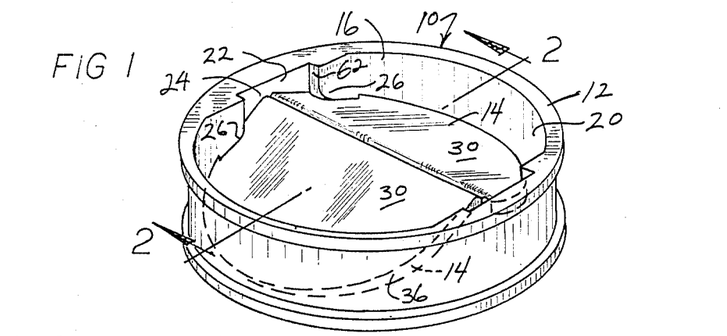
FIG. 1 is a perspective view of a bi-leaflet heart valve embodying various features of the present invention, shown in its closed position.
Figure 2:
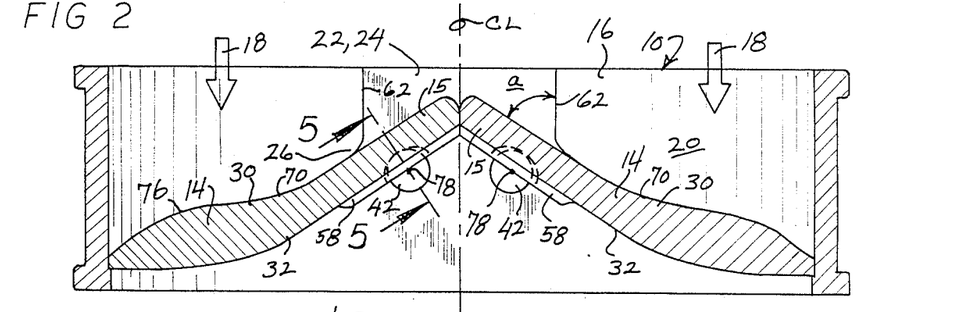
FIG. 2 is an enlarged cross-sectional view of the heart valve taken along the line 2—2 of FIG. 1.
Figure 3:
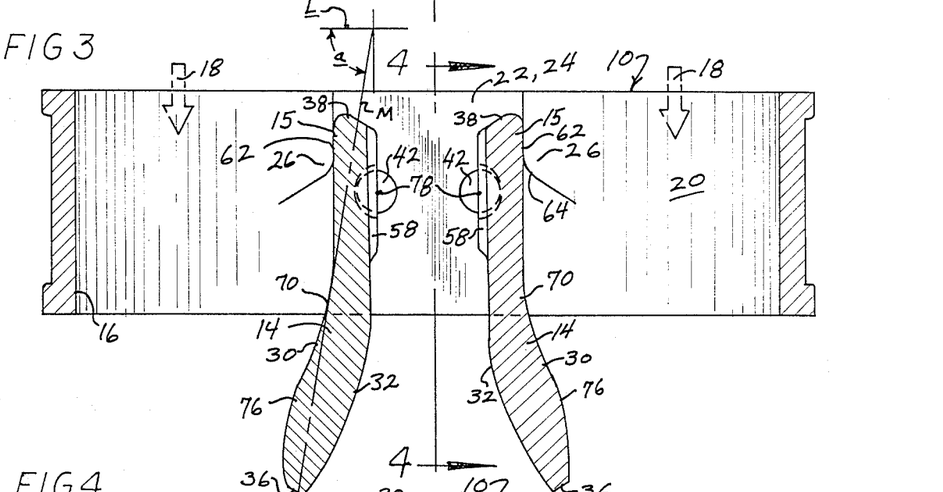
FIG. 3 is a cross-sectional view similar to that of FIG. 2, but showing the valve in an open position.

Referring initially to FIGS. 1–5, heart valve 10 includes a generally annular valve body 12, and carries a pair of pivoting valve occluders or leaflets 14, which open and close to control the normal flow of blood in the downstream direction of arrows 18 (see FIGS. 2 and 3). Blood flows through passageway 16 which is defined by a generally cylindrical interior surface 20 of body 12. Cylindrical interior surface 20 is interrupted by an opposed pair of recesses 22 which receive leading portions of the leaflets 14 when the leaflets are in a fully opened position, such as that illustrated in FIG. 3. The recesses 22 are defined, in part, by a relatively flat endwall 24, in cooperation with pairs of curved surface regions 26.

Referring now to FIGS. 2 and 3, leaflets 14 have an upstream or inflow surface 30 and an opposed downstream or outflow surface 32. With the cross-sectional views of FIGS. 2 and 3, which are taken along the central, major axis of the leaflets, it is apparent that the cross-sectional thickness of the leaflets varies considerably from one end of the leaflet to the other. As will be seen, this is due to a unique three-dimensional composite curvature formed by a cooperation of the leaflet inflow and outflow major surfaces.

The leaflets 14 have a major arcuate edge 36 (see especially FIG. 4), which is located at the trailing portions of a fully opened leaflet. A minor edge 38 is located at the opposite, leading end of the leaflet (again, assuming a leaflet in an opened position). The curved major edge 36 is preferably arcuate in configuration, and the minor edge 38 is preferably of a straight-line configuration so as to present a relatively flat mating surface to the opposing leaflet.

Figure 4:
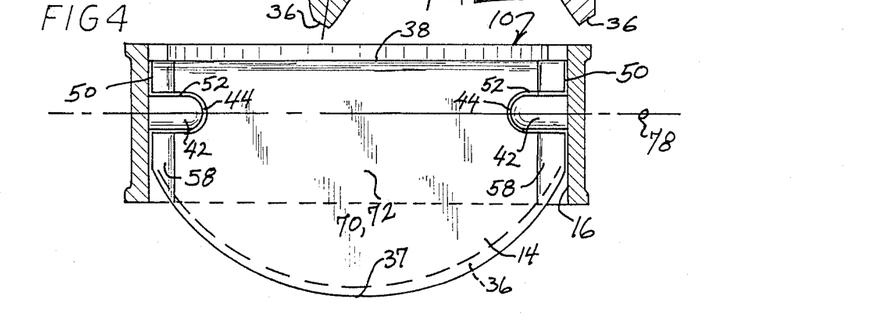
FIG. 4 is a cross-sectional view, reduced in scale, taken along the line 4—4 of FIG. 3.
Figure 5:
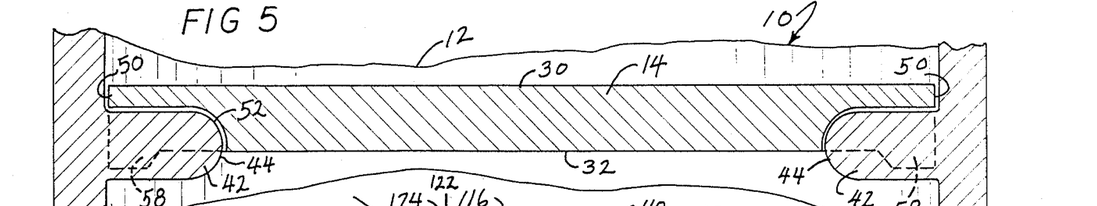
FIG. 5 is an enlarged, fragmentary, cross-sectional view taken along the line 5—5 of FIG. 2.

Referring to FIGS. 4 and 5, leaflet 14 includes a pair of opposed, lateral edges 50 which are interposed between the major arcuate mating edge 36 and the minor straight-line mating edge 38. The lateral edges 50 are preferably of a flat or straight line configuration and provide a minimal clearance with the endwall 24 of valve body 12. Pairs of opposed pivot posts 42 extend from the interior surface 16, with one pivot post located adjacent each end of the minor mating edge 38, overlying the leaflet lateral edges 50. The pivot posts 42 have cylindrical body portions with rounded, free ends.

Pairs of recesses 52 are formed in each leaflet 14, and extend from the lateral edges 50 thereof. The recesses 52 have a shape complementing that of the pivot posts 42, but are slightly larger, so as to provide a low friction pivotal mounting for leaflets 14. The recesses 52 preferably extend throughout most of the length of the pivot posts, but receive only about half thereof at any given time during valve operation. As illustrated in FIG. 5, the outflow surface 32 of the open leaflet is generally aligned with a diametrical plane of the pivot posts 42.

In the preferred embodiment, the recesses 52 and the lateral edges 50 of leaflet 14 are preferably spaced small distances from the corresponding adjacent surfaces of valve body 12 so as to allow a washing between the leaflet edges, leaflet recesses and the opposing surfaces of valve body 12 and the pivot posts 42 so as to prevent, at those locations, stagnation which might eventually lead to clotting. Also, oversizing of the leaflet recesses relative to the pivot posts received therein allow a low friction operation of the leaflet as the leaflet moves between its closed and open positions and, thus, eliminates risk of binding of the leaflet in a fully closed, fully opened or some intermediate position. As will be seen, the heart valve constructed according to principles of the present invention provides improved, rapid closing and opening, and the difference in size of the leaflet and valve body and of the leaflet recesses and the pivot posts insures that the improved, rapid closing and opening times will be experienced in a practical embodiment of the heart valve invention.

As will be seen herein, one particular advantage which is attained with the heart valve constructed according to the present invention, is the unique curvatures which contribute to an improved response time of the valve operation. The upstream or leading end portions 15 of the leaflets 14, i.e., those portions adjacent the minor mating edge 38 which is located at the leading end of a leaflet in an open position, have a significantly reduced thickness, as is apparent from the cross-sectional views of FIGS. 2 and 3. In order to strengthen the leaflet lateral edges 50, outwardly protruding strengthening ribs 58 are added at the outflow surface 32 of the leaflet. Because the strengthening ribs 58 increase the cross-sectional profile of the leaflets and thus reduce the flow area when the valve is in an open position, the ribs 58 preferably have a relatively narrow profile (see FIG. 5). Since no significant disadvantages are realized in extending the ribs in the direction of blood flow, the ribs 58 are lengthened to extend between the minor, mating edge 38 and the arcuate, major mating edge 36 of the leaflet to reduce stress concentration in the leaflet body. This feature also simplifies construction of the leaflets 14 and significantly improves the economy of their fabrication by reducing the labor investment required. As will be appreciated by those skilled in the art, the leaflets and heart valve body have relatively simple configurations which are easy to machine and which also provide an improved economical fabrication, in that tolerances of the heart valve components are easily maintained.

The leaflets 14 are pivotally mounted for rotation between closed and opened positions, and it is generally preferred that the opening and closing motions of the leaflets be made as rapid as possible. However, the end points of the leaflet travel must be well defined to prevent contact with body tissue, for example, and, to reduce noise and leaflet wear, the leaflets should not bounce back when contacting seating surfaces defining the end points of their travel. As will now be seen, such advantages are attained with the present invention.

As mentioned above, the curved surface regions are provided in valve body 12, flanking the recesses 22 cooperating with the relatively flat endwalls 24 to confine the leaflets 14. The curved surface regions 26, of the preferred embodiment, include a first portion having a seating surface 62 and a second, generally arcuate portion or fulcrum 64 adjacent thereto which are positioned immediately adjacent to the pivot posts 42. FIG. 3 shows the relatively flat seating surfaces 62 in contact with the inflow surface 30 of leaflets 14 to define the extent of opening of the leaflets, thus fixing one end of their travel. The other end of the leaflet travel is defined by the contacting of the minor, mating surfaces 38 of the leaflets, and/or the contacting of the major, arcuate, mating surfaces 36 with the interior surface 16 of the valve body.

With reference to FIG. 3, seating surface 62 in combination with a pivot post 42, defines the fully opened position of leaflets 14. It is generally desirable to orient the fully opened leaflets for minimum obstruction of the downstream flow through valve body 12. As can be seen in FIG. 3, the leading, generally planar portions 15 of leaflets 14 are oriented generally parallel to the downstream direction of blood flow, generally indicated by arrows 18.

The flat portion of the leaflet provides maximum flow area at the narrowest section (namely the valvular orifice). However, presenting a minimal cross-sectional area of the leaflet to the blood flow is not alone sufficient to minimize the total impedance of the heart valve to blood flowing therethrough. In particular, the flow quality adjacent the inflow and especially the outflow major surface portions of the leaflets plays an important contribution to overall flow impedance. As will now be seen, heart valves constructed according to principles of the present invention present a heretofore unattainable minimal flow impedance by paying careful attention to the construction of the inflow and outflow surface portions of leaflets 14. Also, according to one aspect of the present invention, the angular orientation of the entire leaflet, not just the leading end thereof, plays an important role in performance of the heart valve. As will be seen, the angle of opening of the heart valve leaflets is well controlled, and is made to lie within a specified range.

Referring to FIGS. 2 and 3, the leaflets 14 have a novel three-dimensional composite curvature which provides maximum flow area at the valvular orifice and reduces boundary layer separation adjacent the major leaflet surfaces when the leaflet is in the open position, so as to minimize drag imparted to blood flowing through the heart valve, resulting in excellent blood flow characteristics. The inflow surface 30 of the leaflets has a concave region 70 of two-dimensional curvature, thus resembling a curved sheet. As used herein, a "two-dimensional" surface is one which comprises a plurality of lines lying along a curved plane, each of which is parallel to a straight line axis. Thus, planes including the axis will cut the two-dimensional surface along straight lines, and planes perpendicular to the axis will cut the two-dimensional surface along curved lines. According to other principles of the present invention, the leaflet inflow surface 30 also includes a convex region 76 of generally two-dimensional curvature, downstream of the concave region 70. Convex region 76 is two-dimensional, so as to resemble a sheet or curved plane having a paraboloid, an ellipsoid or some other curved cross sectional shape. In the preferred embodiment, the various portions of the major leaflet surfaces are blended so as to be continuously smooth, without interruptions or discontinuities.

In its broader aspects, the present invention is not limited to particular convex or concave shapes. For example, the convex surface 76 may have more than one radii of curvature and may not have a cross section as simple as an ellipsoid or a paraboloid, but may have other, more complicated configurations as well.

According to another aspect of the present invention, the outflow surfaces 32 of the leaflets 14 preferably have convex surface regions, at least for those portions of the outflow surfaces 32 which oppose the inflow concave regions 70 and the inflow convex regions 76. The leaflets have a maximum thickness where the convex surfaces 32,76 oppose one another, adjacent the trailing end of an opened valve. It will be noted that the opposed convex surfaces do not meet at a line, but rather are truncated by the arcuate, major mating edge 36, which preferably has a substantial thickness to provide a reliable, low noise, reduced leakage mating with the valve body upon valve closing.

The leaflets 14 are characterized, in one aspect, by having concave and convex surfaces 70,76, and 32 of two-dimensional curvature, each of which are curved about lines which are generally parallel to the leaflet pivot axis 78. Preferably, the lines of curvature are all downstream of the pivot axis 78, although such is not always required.

In order to effectively reduce the boundary layer separation on the inflow surface of the leaflet, it has been found helpful to form both concave and convex curvatures of the inflow surface as two-dimensional curvatures. It has also been found helpful to locate the concave region upstream and adjacent the convex surface region. In the preferred embodiment, the concave region 70 is immediately adjacent the convex region 76.

If desired, however, the inflow and outflow surfaces of the leaflets can have three-dimensional curvatures. For example, the edge portions of the leaflet inflow and outflow surfaces can be reduced in thickness, as shown in the alternative monoleaflet embodiment illustrated in FIG. 8. The convex and concave surface portions of the inflow and outflow surfaces of the leaflets can also be bilobate, with lobes laterally adjacent one another (i.e. perpendicular to the downstream direction, for a fully opened leaflet).

As mentioned above, the pivot posts 42 of the preferred embodiment generally comprise cylinders with rounded, free ends. Thus, the pivot posts 42 are oriented along a common central axis which, in the preferred embodiment, comprises the pivot axis of each leaflet. For ready reference, the pivot axes are identified by the numeral 78, and appear as points in the cross-sectional views of FIGS. 2 and 3. With reference to FIG. 4, the pivot axis 78 extends in a straight line between the tips of the free ends of pivot posts 42.

According to another aspect of the present invention, concave region 70 is preferably spaced downstream from the pivot axis 78 of the leaflet when the leaflet is in the open position, such as illustrated in FIG. 3. Further, the concave region 70 is preferably curved about a straight line which is generally parallel to the pivot axis. As mentioned above, the convex regions 76 are preferably located downstream of the concave regions 70 and thus are spaced further from pivot axis 78 than the concave regions 70 are.

According to another aspect of the present invention, the outflow surface convex region is of a two-dimensional curvature, and is also curved about a line generally parallel to the leaflet pivot axis 78. Given the two-dimensional curvature characteristics, the outflow surfaces 32, in their convex portions, resemble a curved sheet. According to the present invention, the convex portion of the outflow surface generally opposes both two-dimensional concave and convex portions of the inflow surface. According to one aspect of the present invention, this combination has been found to provide heretofore unattainable advantages in minimizing impedance to blood flow across the major leaflet surfaces and is believed to accomplish this, in part, by minimizing boundary layer separation from the outflow surface 32 as well as the inflow surface 30.

As can be seen in FIGS. 2 and 3, the thickness of the leaflets 14 is greatest in the region where the outflow and inflow opposite surfaces are constituted by portions having convex curvatures. This is, the thickest portion of the leaflet 14 occurs where convex surfaces 76, 32, directly oppose one another. Changes can be made if desired, without departing from the present invention. For example, the outflow surfaces 32 of the leaflets 14 can be provided with a recess extending in the downstream direction of arrow 18 (assuming the leaflets in a fully opened position) so that the central portion of the mating edge 38 is narrower in thickness than the portions of the mating edge lying adjacent the lateral edges 50. Also, the edges of the leaflets can be reduced in thickness, as long as the three-dimensional composite curvature described above is maintained throughout a substantial portion of the leaflet inflow and outflow major surfaces.

Other variations can also be made. For example, the leading end 15 of the preferred embodiment has a generally planar configuration with a constant thickness. The concave surface portion 70 and/or the convex surface portion 32 can be extended to the minor mating edge 36, or some other varying thickness configuration can be used at the leaflet leading end.

As can be seen by comparing FIGS. 2 and 3, leaflets 14 undergo a controlled angular displacement between their fully closed and fully opened positions. According to one aspect of the present invention, the angle of opening (i.e. the angular orientation of the leaflets when in the opened position) identified by the reference letter a (See FIG. 3) has a value ranging between about 70° and about 89°. Preferably, the angle of opening of the leaflets has a value ranging between about 70° and about 85°, and most preferably, has an angle ranging between about 77° and about 83°.

As used herein, the term "angle of opening" is defined as the angle between a direction perpendicular to that of the flow through the heart valve (see reference character L in FIG. 3) and the midplane of a fully opened leaflet of that valve, where the "midplane of the leaflet" is a flat plane (identified by the reference character M in FIG. 3) which includes the major central axis of the leading edge, located halfway between the upstream and downstream leaflet surfaces, and the major central axis of the trailing edge, located halfway between the upstream and downstream leaflet surfaces. With reference to FIG. 2, the leading edge of the opened leaflet is the minor mating edge 36. The central axis of the leading edge lies midway between the upstream and downstream major surfaces of the leaflet. In the cross-sectional view of FIG. 3, the midplane M can be seen to cut the leading edge 36 of the leaflet at the furthest leading point thereof, which is halfway between the upstream and down surfaces 30,32.

As mentioned, the leaflet major mating edge has a substantial thickness at the trailing end of the opened leaflet, due to truncation of the leaflet upstream and downstream surfaces at that point. The major central axis cutting the trailing edge of the leaflet bisects the major mating edge 36 at its furthest trailing point 37 (see FIG. 4). Thus, the midplane M bisects both the leading and the trailing edges 36,38, at the furthest leading and trailing excursions thereof. The angle of opening a is measured from a line L perpendicular to the flow direction (i.e. arrow 18) and the midplane M. As will be seen, the terms "angle of opening" and "midplane of the leaflet" apply equally well to leaflets having configurations other than those illustrated herein.

Referring to FIG. 2, the centerline CL of the passageway through the valve body lies midway between the pivot axes 78 of the pivot posts disposed adjacent a given recess 22. In the fully opened position illustrated in FIG. 3, the outflow surface regions 32 lie adjacent the centerline CL and the inflow portions of the leaflets 14 extend generally in the downstream direction, parallel to the centerline CL. In the fully closed position, the minor, mating edges 38 of leaflets 14 abut one another. No matter which opening angle is chosen, it is generally preferred that the leaflets are not brought into a directly opposing, generally coplanar relationship, when fully closed, in order to avoid a risk of wedging of the leaflets.

According to one aspect of the present invention, with the valve in a fully opened position, the pivot axis 78 is spaced apart from the centerline CL by a distance not greater than about 15% of the diametrical length of the central passageway of the leaflet body 12, that is, in a direction generally perpendicular to the pivot axis so as to form a straight line between those axes.

With reference to FIGS. 2 and 3, operation of heart valve 10 will now be described. Assuming an initial, fully closed position, such as that illustrated in FIG. 2, when the cardiac cycle reverses, pressure is developed in the direction of arrows 18. Due to the location of the pivot axis 78, a relatively large moment arm is developed between the pivot axis and the center of the arcuate, major mating edge 36. The leaflets 14 then begin to swing in the direction of valve opening, with their minor mating edges 38 being spread apart, and the outflow convex surface regions 32 being advanced toward one another. The reverse curvature of adjacent, but not necessarily immediately adjacent, concave and convex surface regions of the inflow surfaces 30 are believed to provide an improved, reduced turbulence flow during valve opening.

During valve opening, the leaflet recesses 52 are initially pressed against the leading portions of pivot posts 42. As the leaflets approach a more opened position, the area of contact with the pivot posts 42 continuously changes, as the recesses travel around the pivot posts. Pressure on the pivot posts decreases as the leaflets open, due to reduced leaflet area contacting the blood flow.

Referring now to FIG. 3, the opening movement of the leaflets is stopped when the inflow surfaces 30 thereof contact the seating surfaces 62 of the curved surface regions 26. The seating surfaces 62 are preferably oriented in a direction parallel to the centerline CL of the valve body so as to orient the inflow portions of the fully opened leaflets in a direction which presents minimal cross-section to the blood flow. Although the configuration of the outflow portion of the fully opened leaflets presents a somewhat increased area of contact with the downstream blood flow, the curvatures of the inflow surfaces reduce boundary layer separation and blood flow drag, and the net result is a reduced impedance to downstream blood flow compared to that obtainable with round leaflet configurations.

Upon a reversal of the cardiac cycle, pressure is developed in an upstream direction, generally opposite that to the arrows 18 of FIGS. 2 and 3. Referring initially to FIG. 3, pressure is developed across the convex surface regions of the leaflet outflow surface 32 causing the convex regions 32 to separate, thus initiating pivoting of the leaflets in a closing direction. Initially, due to the inevitable presence of drag forces on the leaflet surfaces, the leaflets 14 are lifted slightly off of the pivot posts 42 as the leaflets begin their closing movements. As greater portions of the leaflet outflow surfaces 32 enter into the blood stream, the rate of closing increases until the leaflets come to rest in a fully closed position.

With the leaflet in the open position, the leading portion of the leaflet inflow surface 30 contacts the seating surface 62 of the curved surface regions 26. As mentioned above, initial closing forces acting on a fully opened leaflet translate the leaflets in a generally upstream direction, opposite to that of arrows 18. The recesses of the leaflets are lifted off of the pivot posts 42, and the fulcrums 64 of the curved surface regions 26 contact the inflow surface 30 of the leaflets to guide the leaflets during closing. Contact between the leaflet inflow surfaces and the fulcrums 64, generally speaking, comprises a rolling contact with low frictional engagement between the inflow leaflet surfaces and the valve body, and particularly the fulcrum portions thereof. The leaflets come to rest in the fully closed position of FIG. 2, in preparation for reversal of the cardiac cycle and a subsequent opening operation.

According to one aspect of the invention, the closing motion of the leaflets is terminated when their minor mating surfaces 38 converge, concurrent with a contact between the arcuate major surfaces 36 and the inner surface 20 of the valve body. If desired, the lower portions of the curved surface regions 26 can also be configured so as to contact the inflow surfaces 30 of the leaflets to aid in stopping the leaflets from further upstream movement. This is, however, generally not desired, since stopping control of the minor and major mating surfaces of the leaflets has been found to be adequate for the purpose. Further, valve closing, in a valve constructed according to principles of the present invention, has been found to be free of bounce-back and the seating of the leaflets in a fully closed position has been found to be smooth and reliable.

As mentioned above, the opposed convex portions of the inflow and outflow leaflet surfaces are truncated at the arcuate mating edge 36 so as to give the edge a substantial thickness which as will now be seen gives several advantages on valve closing. For example, the increased surface area of the mating edge has a greater cushioning effect when contacting the valve body inner surface. This reduces any noise associated with the valve closing, and, with the valve in a fully closed position, provides an elongated leakage path between the leaflet mating edge and the valve body. In addition to reducing leakage volume, this latter feature is particularly important in reducing cavitation at the inflow surfaces of the closed leaflets, adjacent the arcuate mating edge.

The above description pertains to a first embodiment of a heart valve constructed according to principles of the present invention, the first embodiment being characterized by a bi-leaflet design. Attention will now be drawn to FIGS. 6–8 for a second embodiment of a heart valve according to principles of the present invention, which may be conveniently be characterized as having a monoleaflet construction.

Figure 6:
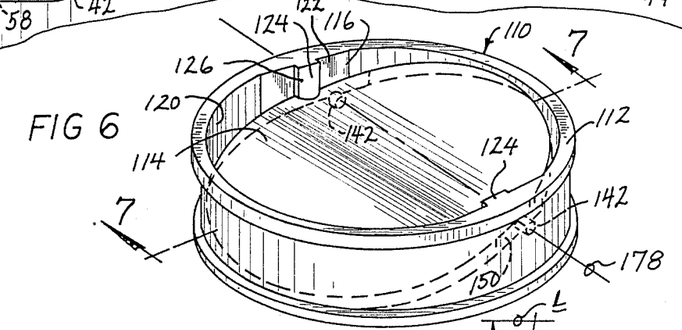
FIG. 6 is a perspective view of an alternative monoleaflet heart valve embodiment illustrating other features of the present invention.
Figure 7:
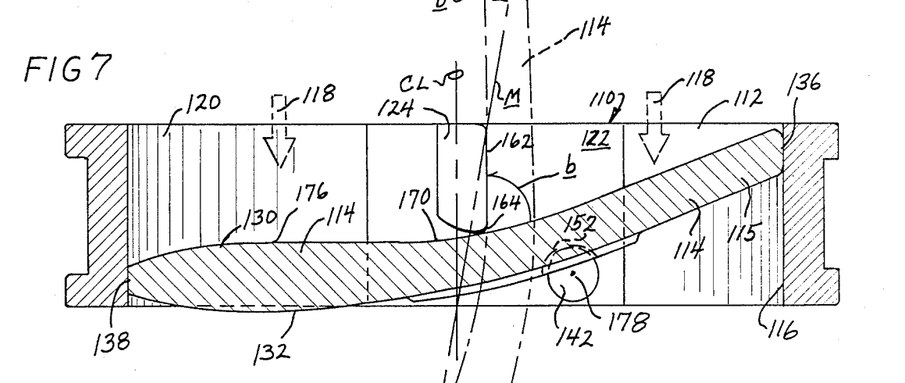
FIG. 7 is an enlarged, cross-sectional view taken along the line 7—7 of FIG. 6.

Referring first to FIGS. 6 and 7, the monoleaflet heart valve is generally indicated at 110. The heart valve 110 includes a generally annular valve body 112 in which is mounted a single leaflet 114. Valve body 112 includes an interior surface 120 which is generally cylindrical in configuration. The heart valve 110 is illustrated in FIG. 6 in a fully closed position. The corresponding cross-sectional view taken along a midplane of the valve body and leaflet is illustrated in FIG. 7 with the leaflet 114 seated against valve body 112 in a fully closed position, with minor and major mating edges 136, 138, contacting the inner surface of the valve body. In the preferred embodiment, the inner surface 120 of the valve body is generally cylindrical, and in order to provide a complete closure in the closed position of the valve, the minor and major mating edges 136, 138, respectively, cooperate to form a generally ellipsoidal outer periphery which mates with the inside surface 120. Although not necessary, it is generally preferred that flat edges 150 be provided adjacent the pivot mounting of the leaflet, and such is a departure from an otherwise completely ellipsoidal outer peripheral configuration.

Valve body 112 further includes guide members 124 which protrude into the interior of valve body 112. Curved surface regions 126 are formed on the outer surfaces of guide members 124, and are configured to attain numerous advantages, as will be explained herein. Except for the intrusion of guide members 124 into the interior of the valve body passageway 116, the passageway is uninterrupted.

Figure 8:
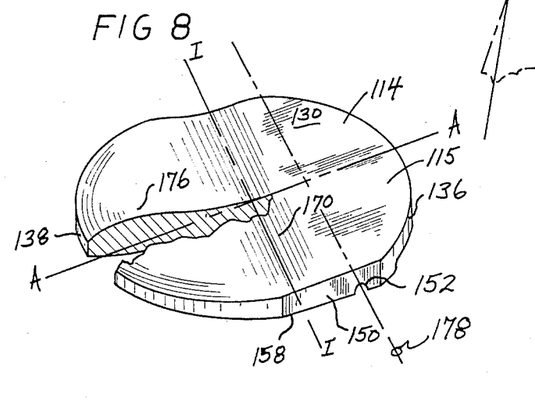
FIG. 8 is a perspective view, shown partly broken away, of the leaflet of FIGS. 6 and 7.

With additional reference to FIG. 8, the leaflet 114 has an upstream or inflow surface 130 and a downstream or outflow surface 132. Leaflet 114 preferably has a pair of opposed lateral edges 150 located adjacent a relatively flat upstream or leading end 115 of the leaflet as can be seen in FIG. 7. As in the first preferred embodiment, the lateral edges 150 are generally flat. The leading end of the preferred embodiment has a relatively constant cross section. The opposed, trailing end of an opened leaflet has a changing, thickened cross section.

A pair of post-receiving recesses 152 extend toward each other, penetrating the leaflet 114 and extending from the lateral edges 150 thereof. A pair of pivot posts 142 receive cantilever support from valve body 112 at the flat surface regions 122 thereof and extend into the valve body passageway 116. The pivot posts are preferably colinearly aligned along a pivot axis 178 (see FIG. 6). The pivot posts of the preferred embodiment have cylindrical body portions with rounded, preferably free ends. The pivot axis preferably does not lie along a diameter of the valve body, but rather is shifted to one side thereof. Referring to FIG. 7, for example, the pivot axis is preferably spaced approximately one-third the diametrical distance from the right hand end of the annular valve body.

The recesses 152 extend into the leaflet 114 from the outflow surface 132 thereof. In the preferred embodiment, support ribs 158 extend from the outflow surface 132 of the leaflet. Preferably, the support ribs 158 are relatively narrow, and cover only a portion of the pivot posts 142. The recesses 152 have the same general shape as the pivot posts 142 but are dimensioned slightly larger than the pivot posts to provide a slight clearance for a wash of blood flow across the recess and pivot post surfaces. The recesses 152 are dimensioned so as to receive a portion of the pivot posts 142. In the preferred embodiment, the pivot posts 142 are generally cylindrical, and only a semi-cylinder portion of the pivot post is received in the leaflet recess at any given time during leaflet operation. As the leaflets pivot about the pivot post 142, different portions of the pivot post are received in the recess and thus, any wear that might be experienced by the pivot post is spread over an enlarged area.

Referring again to FIG. 7, the guide members 124 have a curved surface portion with a first portion which is generally flat and includes a seating surface 162 and an adjacent generally arcuate camming surface or fulcrum portion 164. As will be seen herein, the surfaces 162, 164 of guide member 124 contact the inflow surface 130 of the leaflet during valve operation so as to guide the leaflet and control its movement.

According to one aspect of the present invention, inflow leaflet surface includes a concave region 170 which extends from the minor mating edge 136 to a point downstream of the pivot post 142 and pivot axis 178 thereof, assuming a leaflet in a fully opened position. A generally convex surface region 176 is located downstream of the concave region 170. Again, the term "downstream" assumes a leaflet in a fully opened position such as that illustrated in phantom in FIG. 7. In the preferred embodiment, the concave and convex surface regions 170, 176 are located immediately adjacent one another, but if desired, the concave and convex surface regions can be separated by an intermediate surface region. As with the first embodiment, the concave and convex surface regions 170, 176 are preferably of a two-dimensional curvature, being curved about lines which are generally parallel to the leaflet pivot axis 178. The leaflet 114, constructed according to principles of the present invention is, in one aspect, characterized by a maximum thickness in the downstream regions of the fully opened leaflet where the convex surfaces 130, 132 oppose one another. As in the first, bileaflet embodiment, it is generally preferred that the convex surfaces do not meet at a line, but rather are truncated by an edge 138 of substantial thickness.

According to another aspect of the present invention, the outflow surface 132 of leaflet 114 is generally convex, at least in that portion directly opposite the concave and convex surface regions of the inflow leaflet surface. Three-dimensional composite curvatures of the leaflet 114 result from the cooperation of the uniquely configured inflow and outflow surface configurations of the leaflet to provide heretofore unattainable improved low resistance to blood flow through the leaflet. In particular, the inflow and outflow surfaces of the leaflet have been found to have a reduced boundary layer separation, thus resulting in decreased drag forces on the blood flow when the leaflet is in a fully opened, maximum flow position. The improved reduced boundary layer separation on the outflow surface 132 has been found to be particularly important in reducing thrombus formation potential and reducing drag on blood flow through the leaflet 110.

The leaflet major axis is noted in FIG. 8 by the reference line A—A. As can be seen, the leaflet 114 is symmetric about the line A—A. The minor axis I—I of the leaflet 114 is also illustrated in FIG. 8. The pivot axis 178 of the leaflet extends generally parallel to the minor axis I—I, but is spaced upstream therefrom (assuming a leaflet in a fully opened position). As can be seen from the above description, the leaflet 114 is not symmetric about the minor axis, and in particular, has an enlarged thickness located to one side (downstream) of the minor axis.

The leaflet 114 is illustrated in solid lines in FIG. 7 in a fully closed position, and in phantom lines in a fully opened position. The fully closed position is defined, at least in part, by the engagement of the minor mating edge 136 and the major mating edge 138 of the leaflet with the interior surface 120 of valve body 112 and the inflow surface 130 contacts the arcuate portion 164 of guide member 124 when the leaflet is in a fully closed position.

In the fully opened position of the valve, the inflow surface of leaflet 114 contacts the flat seating surface 162 of guide member 124. The leaflet 114 pivots about the pivot posts 142 between its closed and opened positions. During portions of the closing operation, the inflow surface 130 of leaflet 114 rolls about the arcuate portion 164 of guide member 124. According to one aspect of the present invention, the angle of opening b of the fully opened leaflet is carefully controlled by a cooperation between the surfaces of guide member 124, the pivot posts 142 and the mating edges 136, 138 of leaflet 114. For example, the guide member 124 is located adjacent pivot post 142, in close proximity to the inflow surface 130 of leaflet 114. The angle of opening b of the monoleaflet embodiment, measured between line L and midplane M is defined in a manner similar to that of the angle a described above with reference to the bileaflet embodiment.

In the fully closed position, the leaflet mating edges 136, 138 engage the interior surface 120 of valve body 112, as described above, and the inflow surface 130 of leaflet 114 contacts the outer surface 164 of guide member 124. Upon valve opening, the leaflet 114 pivots about pivot post 142 with the guide surface contacting the inflow surface 130 of the leaflet. Leaflet opening continues until the inflow surface 130 of the leaflet contacts the seating surface 162 of guide member 124. Thus, the angle of opening b is carefully defined between the leaflet fully opened and fully closed positions. The angle of opening b preferably ranges in value between about 70° and about 85° and most preferably, it ranges between about 77° and about 83°.

Assuming a leaflet in a fully closed initial position, operation of the leaflet is initiated with a reversal in the cardiac cycle, wherein blood pressure is developed in a downstream direction, that indicated by arrows 118 in FIG. 7. Pressure is developed against the inflow surface 130 of leaflet 114, pressing the recess 152 of the leaflet against the pivot posts 142, and developing a moment arm extending from pivot axis 178 to the major mating edge 138 of the leaflet. Rotation of the leaflet is then initiated in a direction causing leaflet opening, with recess 152 wiping across different portions of pivot posts 142.

As the leaflet approaches the fully opened position indicated in phantom in FIG. 7, the pressure of the leaflet recess on the pivot post 142 is relaxed to some extent, owing to a desired clearance between the leaflet recess 152 and the pivot post 142. Opening of the leaflet is terminated when the inflow surface 130 of the leaflet contacts the seating surface 162 of the guide member 124.

With a reversal in the cardiac cycle, blood pressure is developed in a generally upstream direction, that opposite the direction indicated by arrows 118 of FIG. 7. Initially, due to inevitable drag forces against the outer surfaces of leaflet 114, the leaflet is raised in an upstream direction, with the surfaces of recess 152 being lifted off of the pivot post 142. With clearances between the recess and pivot post, the leaflet is free to "float" with the inflow surface 130 of the leaflet coming into contact with guide member 124 and, in particular, the camming surface 164 thereof. With rotation of leaflet 114 in a direction for leaflet closing, the inflow surface 130 of the leaflet rolls across the arcuate surface 164 of the guide member. The rolling contact between the leaflet inflow surface and the arcuate surface 164 of the guide member continues until the leaflet assumes a fully closed position, with the minor and major mating edges 136, 138 seating against the inside surface of the valve body. As in the first embodiment, the opposed convex surfaces of the leaflet inflow and outflow surfaces are truncated to form a mating edge 138 of substantial thickness, as opposed to meeting at a curved line. The enlarged mating edge 138 cushions the valve closing, reducing noise, and reduces leakage volume and leakage flow velocity thus eliminating cavitation at the inflow surface of the leaflet.

Modifications to the above leaflet design are possible. For example, the leading portion 115 of leaflet 114, which has a generally planar configuration, with opposed generally planar inflow and outflow surface portions, can be altered to have a varying thickness. Alternatively, the concave surface region 170 of the inflow surface and the convex configuration of the outflow surface 132 can be extended to the minor mating edge 136.

It can be seen from the above that the embodiments of a heart valve constructed according to the principles of the present invention obtain numerous advantages, including a heretofore unavailable economical manufacture of the heart valve components. The cooperation of the inflow and outflow surface configurations of the heart valve leaflet provide unprecedented reductions in drag on blood flow through the fully opened heart valve. The surface configurations of the leaflets are not, however, difficult to machine, and preferably consist of combinations of two-dimensional curvatures.

The description of the present forms of the invention having been described by way of example, it is anticipated that variations of the described forms of the apparatus may be made without departing from the invention and the scope of the appended claims.

What is claimed is:

1. A prosthetic heart valve for allowing blood flow therethrough in a downstream direction, which valve comprises
    a generally annular valve body having an interior surface defining a central passageway through which blood flows,
    a pair of occluders proportioned to be pivotally received within said valve body and to move between an open position wherein downstream flow of blood is permitted and a closed position wherein the reverse flow of blood in an inflow direction is blocked, said occluders each having a pair of opposite lateral edges respectively extending between a minor mating edge and a major arcuate edge and having major inflow and outflow surfaces,
    cooperative pivotal mounting means incorporated in said occluders in the regions of each lateral edge and in said valve body in its interior surface region which cooperate to establish generally pivotal movement of said occluders about a pair of parallel pivot axes,
    said occluders each having an inflow surface formed with a concave region of two-dimensional curvature and with a generally convex region of two-dimensional curvature, said concave surface region being spaced downstream from said pivot axis in said open position and being curved about a straight line which is generally parallel to said pivot axis, said convex region being spaced further from said pivot axis than said concave region, and
    said occluders being installed in said annular valve body and constructed so that said occluders have an angle of opening of about 70° to about 85° in said fully open position with said outflow surface regions lying generally adjacent the centerline through said central passageway, and so that, in the closed position, said mating edges of said occluders generally abut each other and said arcuate edges of said occluders abut said valve body interior surface.

2. A heart valve according to claim 1 wherein each said occluder outflow surface is formed with convex surface regions which are located in the same regions of said occluder wherein said inflow convex region and said inflow concave region are located.

3. A heart valve according to claim 2 wherein said outflow surface convex region is of two-dimensional curvature, being curved about a line parallel to the occluder pivot axis.

4. A heart valve according to claim 3 wherein said radius of curvature of said convex outflow surface region decreases in a direction distal from said pivot axis.

5. A heart valve according to claim 1 wherein the thickness of each said occluder is greatest in the region wherein the outflow and inflow opposite surfaces are constituted by portions of the respective convex surface regions.

6. A heart valve according to claim 1 wherein said cooperative pivotal mounting means includes pairs of pivot posts protruding from said interior surface of said annular valve body and complementary cavities formed in said outflow surface regions of said occluders for receiving said pivot posts.

7. A heart valve according to claim 6 wherein retaining means having a curved surface region is provided which protrudes from said interior surface of said valve body, said retaining means being located in adjacent facing relationship to said pivot posts so that said curved surface region serves as a stop for said occluders in the open position and serves as a fulcrum against which said occluders bear in moving from the open position to the closed position.

8. A heart valve according to claim 7 wherein said curved surface region includes a flat surface portion comprising said stop and an arcuate surface portion comprising said fulcrum, said flat and said arcuate surface portions positioned to contact the inflow surface of said occluder.

9. A heart valve according to claim 1 wherein said angle of opening of said occluder is between about 77° and about 83°.

10. A heart valve according to claim 1 wherein said pivot axis is located a distance from said centerline not greater than about 15% of the length of the diameter of said central passageway taken in a direction perpendicular to said pivot axis.

11. A prosthetic heart valve for allowing blood flow therethrough in a downstream direction, which valve comprises
    a generally annular valve body having an interior surface defining a central passageway through which blood flows,
    occluder means proportioned to be pivotally received within said valve body and to move between an open position wherein downstream flow of blood is permitted and a closed position wherein the reverse flow of blood in an inflow direction is blocked, said occluder means having a pair of opposite lateral edges respectively extending between a minor mating edge and a major arcuate edge and having major inflow and outflow surfaces,
    cooperative pivotal mounting means incorporated in said occluder means lateral edge and in said valve body in its interior surface region which cooperate to establish generally pivotal movement of said occluder means about a pivot axis,
    said occluder means having an inflow surface formed with a concave region of two-dimensional curvature and with a generally convex region of two-dimensional curvature, said concave surface region being spaced downstream from said pivot axis in said open position and being curved about a straight line which is generally parallel to said pivot axis, said convex region being spaced further from said pivot axis than said concave region, and
    said occluder means being installed in said annular valve body so as to have an angle of opening of about 70° to about 85° in said fully open position, and so that, in the closed position, said major arcuate edge of said occluder means abuts said valve body interior surface.

12. A prosthetic heart valve for allowing blood flow therethrough in a downstream direction, which valve comprises
    a generally annular valve body having an interior surface defining a central passageway through which blood flows,
    a pair of occluders proportioned to be pivotally received within said valve body and to move between an open position wherein downstream flow of blood is permitted and a closed position wherein the reverse flow of blood in an inflow direction is blocked, said occluders each having a pair of opposite lateral edges respectively extending between a minor straight mating edge and a major arcuate edge and having generally opposed major inflow and outflow surfaces,
    cooperative pivotal mounting means incorporated in said occluders in the regions of each lateral edge and in said valve body in its interior surface region which cooperate to establish generally pivotal movement of said occluders about a pair of parallel pivot axes,
    said occluder inflow surfaces each including a concave region of two-dimensional curvature and a generally convex region of two-dimensional curvature, said concave and said convex regions curved about spaced straight lines which are generally parallel to and downstream of said pivot axis in said open position, said convex region being spaced further from said pivot axis that said concave region,
    said occluder outflow surfaces each including a convex region of two-dimensional curvature, curved about a line parallel to and downstream of the occluder pivot axis in said open position, said outflow surface convex region generally opposing said concave and said convex regions of said occluder inflow surfaces so as to form therewith an occluder of maximal thickness adjacent the major mating edge, and
    said occluders being installed in said annular valve body and constructed so that said occluders have an angle of opening of about 70° to about 85° in said fully open position with said outflow surface regions lying generally adjacent the centerline through said central passageway, and so that, in the closed position, said mating edges of said occluders generally abut each other and said arcuate edges of said occluders abut said valve body interior surface.

13. A heart valve according to claim 12 wherein said occluders include generally planar opposing inflow and outflow surface portions upstream of said pivot axis.

14. A prosthetic heart valve for allowing blood flow therethrough in a downstream direction, which valve comprises
    a generally annular valve body having an interior surface defining a central passageway through which blood flows,
    occluder means proportioned to be pivotally received within said valve body and to move between an open position wherein downstream flow of blood is permitted and a closed position wherein the reverse flow of blood in an inflow direction is blocked, said occluder means each having a pair of opposite lateral edges respectively extending between a minor straight mating edge and a major arcuate edge and having generally opposed major inflow and outflow surfaces, cooperative pivotal mounting means incorporated in said occluder means lateral edges and in said valve body interior surface region which cooperate to establish generally pivotal movement of said occluder means about a pivot axis, said occluder inflow surface including a concave region of two-dimensional curvature curved about a straight line which is generally parallel to and downstream of said pivot axis in said open position and a generally convex region of two-dimensional curvature, curved about a straight line which is generally parallel to said pivot axis, said convex region being spaced further from said pivot axis then said concave region, said occluder outflow surface including a convex region of two-dimensional curvature, curved about a line parallel to the occluder pivot axis, said outflow surface convex region generally opposing said concave and said convex regions of said occluder inflow surfaces so as to form therewith an occluder of maximal thickness adjacent the major mating edge, and said occluder means being installed in said annular valve body and constructed so that said occluder means has an angle of opening of about 70° to about 85° in said fully open position with said outflow surface region lying generally adjacent the centerline through said central passageway, and so that, in the closed position, said mating edges of said occluder means generally abut said valve body interior surface.

* * * * *

UNITED STATES PATENT AND TRADEMARK OFFICE
CERTIFICATE OF CORRECTION

PATENT NO. :   4,872,875

DATED      :   October 10, 1989

INVENTOR(S):   Ned H. C. Hwang

It is certified that error appears in the above-identified patent and that said Letters Patent is hereby corrected as shown below:

Column 10, line 33, delete the word "be" (second occurrence).

Column 12, line 27, after the word "can" insert the word --now--.

IN THE CLAIMS:

In Claim 1, line 11, substitute the word "upstream" for the word --inflow--.

In Claim 11, line 11, substitute the word --upstream-- for the word "inflow".

In Claim 12, line 11, substitute the word --upstream-- for the word "inflow" and on line 39, substitute the word --arcuate-- for the word "mating".

UNITED STATES PATENT AND TRADEMARK OFFICE
CERTIFICATE OF CORRECTION

PATENT NO. : 4,872,875

DATED : October 10, 1989

INVENTOR(S) : Ned H.C. Hwang

It is certified that error appears in the above-identified patent and that said Letters Patent is hereby corrected as shown below:

Claim 14, line 11, substitute the word --upstream-- for the word "inflow"; line 12, delete the word "each"; line 37, substitute the word --arcuate-- for the word "mating"; line 42, change the word "outflow" to the word --inflow--; and line 45 substitute the words --major arcuate-- for the word "mating".

Signed and Sealed this

Fourth Day of June, 1991

*Attest:*

HARRY F. MANBECK, JR.

*Attesting Officer*  Commissioner of Patents and Trademarks